United States Patent [19]

Sauer et al.

[11] Patent Number: 5,611,794

[45] Date of Patent: Mar. 18, 1997

[54] CLAMP FOR APPROXIMATING TISSUE SECTIONS

[75] Inventors: Jude S. Sauer, Pittsford; Theodore J. Tiberio, Hilton, both of N.Y.

[73] Assignee: LaserSurge, Inc., Rochester, N.Y.

[21] Appl. No.: 483,957

[22] Filed: Jun. 6, 1995

Related U.S. Application Data

[63] Continuation of Ser. No. 958,277, Oct. 8, 1992, abandoned, which is a continuation-in-part of Ser. No. 595,871, Oct. 11, 1990, abandoned.

[51] Int. Cl.$^6$ .................................................. A61B 17/36
[52] U.S. Cl. ............................ 606/8; 606/153; 606/213; 606/216
[58] Field of Search ........................... 606/8, 10–12, 606/151–158, 191, 213, 216; 623/1, 11, 12

[56] References Cited

U.S. PATENT DOCUMENTS

| | | | |
|---|---|---|---|
| 1,151,300 | 8/1915 | Soresi | 606/153 |
| 2,965,900 | 12/1960 | Inokouchi | 606/153 |
| 3,316,914 | 2/1963 | Collito | 606/153 |
| 3,683,926 | 8/1972 | Suzuki | 606/154 |
| 4,165,747 | 8/1979 | Bermant | 606/153 |
| 4,263,495 | 4/1981 | Fujita et al. | 219/121.63 |
| 4,483,339 | 11/1984 | Gillis | 623/1 |
| 4,625,724 | 12/1986 | Suzuki et al. | 606/153 |
| 4,633,870 | 7/1987 | Sauer | 606/8 |
| 4,652,264 | 3/1987 | Dumican | 623/1 |
| 4,854,320 | 8/1989 | Dew et al. | 606/8 |
| 4,892,098 | 1/1990 | Sauer | 606/18 |
| 4,917,090 | 4/1990 | Berggren et al. | 606/153 |

FOREIGN PATENT DOCUMENTS 2630904   11/1989   France .

OTHER PUBLICATIONS

Okada et al. "A New Method Of Vascular Anastomosis By Low Energy $CO_2$ laser" Aug. 23, 1985.

*Primary Examiner*—Angela D. Sykes
*Assistant Examiner*—Michael Peffley
*Attorney, Agent, or Firm*—Cumpston & Shaw

[57] ABSTRACT

A surgical apparatus for energy welding or otherwise joining two segments of living tissue, usually tubular in structure, comprising, means for clamping the first tissue section, means for clamping the second tissue section, means for moving one of said clamping means toward said other clamping means to bring the first and second sections into abutting relationship to form a seam. Means for transmitting energy to the seam may be provided to weld together the first and second sections. The means for clamping the first section comprises a first pair of opposed arms and the means for clamping the second section comprises a second pair of opposed arms, wherein at least one of said arms of each said pair of arms is pivotably connected to said opposing arm. The energy transmitting means comprises first and second housing sections adapted to be placed over opposing sides of the clamping means wherein each of the housing sections has a plurality of energy transmissive elements extending therethrough. The distal end of the energy transmissive elements terminates near the seam.

33 Claims, 13 Drawing Sheets

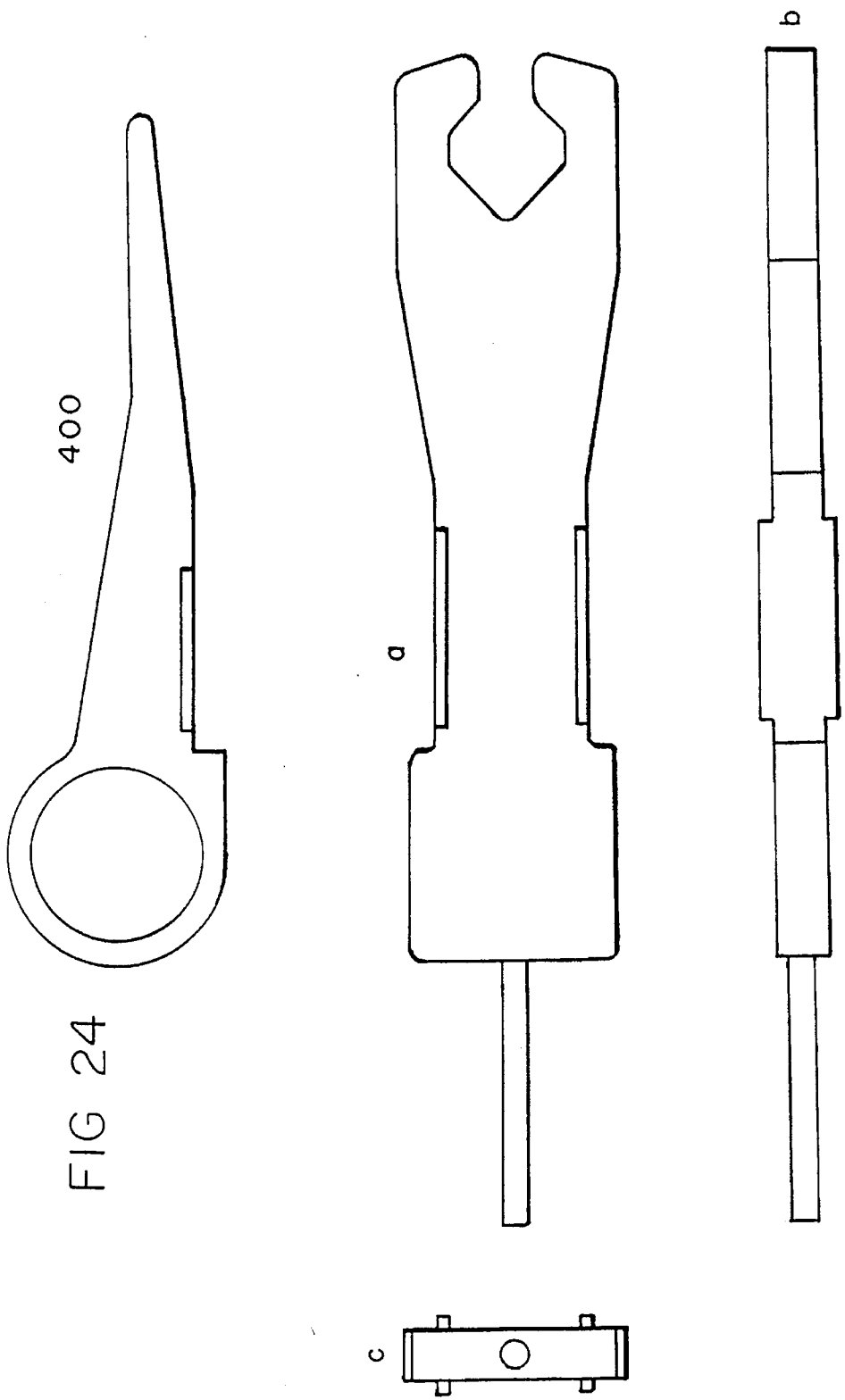

CLAMP FOR APPROXIMATING TISSUE SECTIONS

CROSS REFERENCE TO RELATED APPLICATION

This is a continuation of application Ser. No. 07/958,277 filed on Oct. 8, 1992 (now abandoned), which is a continuation-in-part of applicant's application, U.S. Ser. No. 07/595,871, filed on Oct. 11 1990 (now abandoned), and entitled Clamp for Approximating Tissue Sections incorporated herein by reference.

BACKGROUND OF THE INVENTION

1. Field of the Invention

This invention relates to tissue welding and more particularly to a method and apparatus for holding tissue sections in apposition and compression during application of energy to weld the sections together.

2. Description of the Related Art

Conventional surgical techniques typically require the use of sutures or staples to construct surgical connections that provide functional communication between living tissue structures. These surgical connections are generally referred to as "anastomoses". Anastomoses between cylindrical, especially tubular (i.e. hollow) structures are of significant clinical importance.

The problems associated with the utilization of sutures or staples are numerous. First, it is often time consuming and technically difficult to perform anastomoses by sutures or staples. This not only results in increased costs to the patient, a factor which cannot be overlooked as the current trend of skyrocketing health care costs continues, but creates a wide discrepancy in performance between surgeons, especially between experienced and novice surgeons. Second, the use of sutures and staples also means the introduction of "foreign bodies" which can cause trauma, inflammatory and immune response, and other adverse reactions due to the actual introduction as well as the prolonged presence of these foreign materials. Inflammation can actually cause a decrease in tensile strength and bursting strength of an anastomosis. Inadequate anastomoses pose a severe health risk to the patient if the sutured tubes or organs become sufficiently weak that they separate.

In an attempt to overcome these problems associated with sutures and staples, work recently began on the use of laser energy for welding the tubular and other types of tissue. It was discovered that properly applied laser light thermally induces intrinsic tissue changes which immediately produce hermetically sealed, strong bonds between the tissue. Such laser welding may also result in increased collagen synthesis, rapid restoration of tissue function, and enhanced healing. Additionally, advantageous for younger patients, laser welding allows the growth of welded seams as body size increases.

Thus, not only does laser tissue welding avoid the adverse effects associated with introducing foreign particles, i.e. sutures and staples, into the patient's body by avoidance of needle trauma and minimization of inflammatory and immune response, but laser welding can actually optimize the strength and functional characteristics of the anastomoses. Although laser energy is specifically addressed herein, the present invention contemplates energy sources of a broader magnitude including all applications of energy sufficient to affect tissue welding.

Still further, more automated energy tissue welding advantageously does not require the skill and time-consuming labor of the surgeon which is necessary for suturing and stapling. In fact, once the equipment is properly placed by the surgeon, a nurse or technician can simply switch the equipment on to provide the energy necessary to weld the tissue. This energy delivery technique requires no manual manipulation during the actual welding of the tissue and usually requires less than 10 seconds of welding time. Thus, a mechanical means for holding tissue during welding also provides an increased level of consistency which simply cannot be achieved in the individualized hand-manipulated suturing and stapling techniques or in less automated tissue welding techniques. The automated control of the energy welding parameters, rather than the skill or experience of a particular surgeon, determines the immediate success of the welding as well as the long term holding strength of the anastomosis.

The two essential criteria for successful energy welding are: (1) control of energy delivery and (2) tissue apposition. Control of energy (precision and consistency) is important to ensure that the desired amount of incoming energy is absorbed by the tissue. This means providing consistent energy density at a specific rate (i.e. fluence) over the entire anastomotic seam. Tissue apposition is critical since the ends of the hollow tubular sections to be welded must be in substantial abutment and accurate alignment to ensure that the energy effectively fuses the entire seam formed at the abutment. Substantial abutment also requires compression of the edges of the tubular sections. Deficient apposition can cause leakage or the formation of weak tissue bonds. Inadequate anastomoses can result in separation of the tissue sections, abnormal formation of fibrous tissue (adhesions) or undesired narrowing of the passage between the tubular sections (stenosis). The importance of tissue apposition cannot be overemphasized.

To date, many failed attempts at producing an effective energy anastomosis can be attributed to inadequate tissue approximation. Such inadequate welds have forced surgeons to rely on the use of "stay" sutures to assist in tissue alignment and orientation during welding. Such stay sutures, usually numbering at least three for each anastomosis, are typically left at the wound site and result in all of the accompanying drawbacks and deficiencies enumerated above. Therefore, there exists a need for a way to provide precise apposition of the ends of the tubular tissue sections to be welded as well as a need for maintaining the abutting tissue ends in this position during application of energy to the seam.

An apparatus and method for precisely aligning the tissue to create effective tissue welding would have a virtually limitless number of applications. For example, such apparatus could be used in reversing vasectomies (i.e. a refertilization procedure known as "vasovasostomy") by welding the severed ends of the vas deferens to re-establish communication, or used in fallopian tube anastomoses for reversing surgically-induced sterilization, or repairing defects to help allow women to achieve desired pregnancy. This is especially significant with the current high divorce rate, and the resulting number of remarriages, where many men and women seek to have a second family and thus require reversal of their surgical sterilization. An apparatus and method for performing these techniques by energy welding would provide an efficient, accurate and improved way to reverse sterilization, plus an increased success rate and reduced health risks to the patient. It would also result in increased consistency and decreased surgery time. Additional uses for such energy welding with the aforementioned advantages could include anastomoses for the bowel, ureters, urethra, blood vessels, biliary tissue, etc. In short, an apparatus for maintaining and securing tissue in close apposition and in correct alignment to enable accurate application of energy to weld the tissue sections would provide countless advantages over the prior surgical procedures of suturing and stapling and over the prior hand-manipulated tissue welding techniques.

SUMMARY OF THE INVENTION

The present invention provides an improved method and apparatus for holding two tubular or other types of tissue sections in apposition and compression for energy welding. The apparatus comprises means for clamping one of the tissue sections, means for clamping the other tissue section, and means for moving one of the clamping means towards the other clamping means to bring the two tissue sections into abutting relationship. Means for transmitting energy to the seam to weld together the two tissue sections is provided. The energy used herein can include any appropriate energy capable of joining tissue. In the preferred embodiment electromagnetic energy, such as, for example laser and/or white light is contemplated.

Each clamping means preferably comprises a pair of opposed arms or jaws wherein at least one of the arms is pivotably connected to the opposing arm and is pivotable from an open position spaced from the opposing arm to a closed position overlying the opposing arm. The apparatus also preferably and advantageously has anchor means in the form of a swivelable retainer mounted to one of the arms of each pair of arms for holding the opposing arms together in the closed position. In a second embodiment the anchor means is preferably in the form of a slidable anchor barrel overlying one of the arms of each pair of arms for holding the pair of arms together in the closed position. The arms are preferably mounted substantially perpendicular to an axle and one of the pairs of arms slides longitudinally along said axle towards the other pair of arms to bring the tissue sections into apposition.

The second embodiment typically comprises a first body section comprising a first pair of arms functionally attached to an axle housing and a second body section comprising a second pair of arms functionally attached to an axle. Preferably the arms do not move relative to the longitudinal axis of the respective axle housing or axle. Typically the axle housing and axle are adapted to fit together to maintain end portions of the first pair of arms at one or more specific distances relative to end portions of the second pair of arms. Moreover the axle housing and axle are adapted to align and position the end portions of the first and second pairs of arms such that tissue held in the first pair of arms may be welded or otherwise connected to tissue held in the second pair of arms.

The energy transmitting means preferably comprises first and second housing sections adapted to be placed over opposing sides of the clamp wherein each of the housing sections has a plurality of energy transmissive elements extending therethrough. In a second embodiment the housing section is one piece and adapted to fit into a slot on the clamp. The distal end of the elements terminates near the seam formed at the abutment of the tubular tissue sections. The proximal end of the transmissive elements is connected to an external source. The transmissive elements preferably extend towards the seam to simultaneously transmit energy radially onto substantially the entire circumferential portion of the seam.

The present invention also comprises a method for holding two sections of living tissue in close approximation for energy welding comprising clamping one section of the tissue between a first pair of jaws of a clamp, clamping another section of the tissue between a second pair of jaws of the clamp, and moving one of the pairs of jaws towards the other pair to bring the two tissue sections into abutting relationship. The step of moving one pair of jaws preferably comprises the step of sliding the pair of jaws longitudinally along an axle on which said jaws are mounted.

Sufficient energy is applied to the seam formed at the abutting portion of the sections to weld them together. This is achieved by placing a first housing section on one side of the clamp, placing a second housing section on the opposing side of the clamp to interfit with the first housing section, wherein each housing section contains an energy transmissive conduit. Both the housing sections and the clamp are removed after the tissue sections are welded.

BRIEF DESCRIPTION OF THE DRAWINGS

The present invention will be more fully appreciated as the same becomes better understood from the following detailed description of the present invention when considered in connection with the accompanying drawings in which:

FIG. 24 is a side view of an alignment tool; and,

FIGS. 25a, b, and c are top, end and side views, respectively, of an ExoScope™ housing to be used with the present invention.

DETAILED DESCRIPTION OF THE PREFERRED EMBODIMENTS

Figure 1:
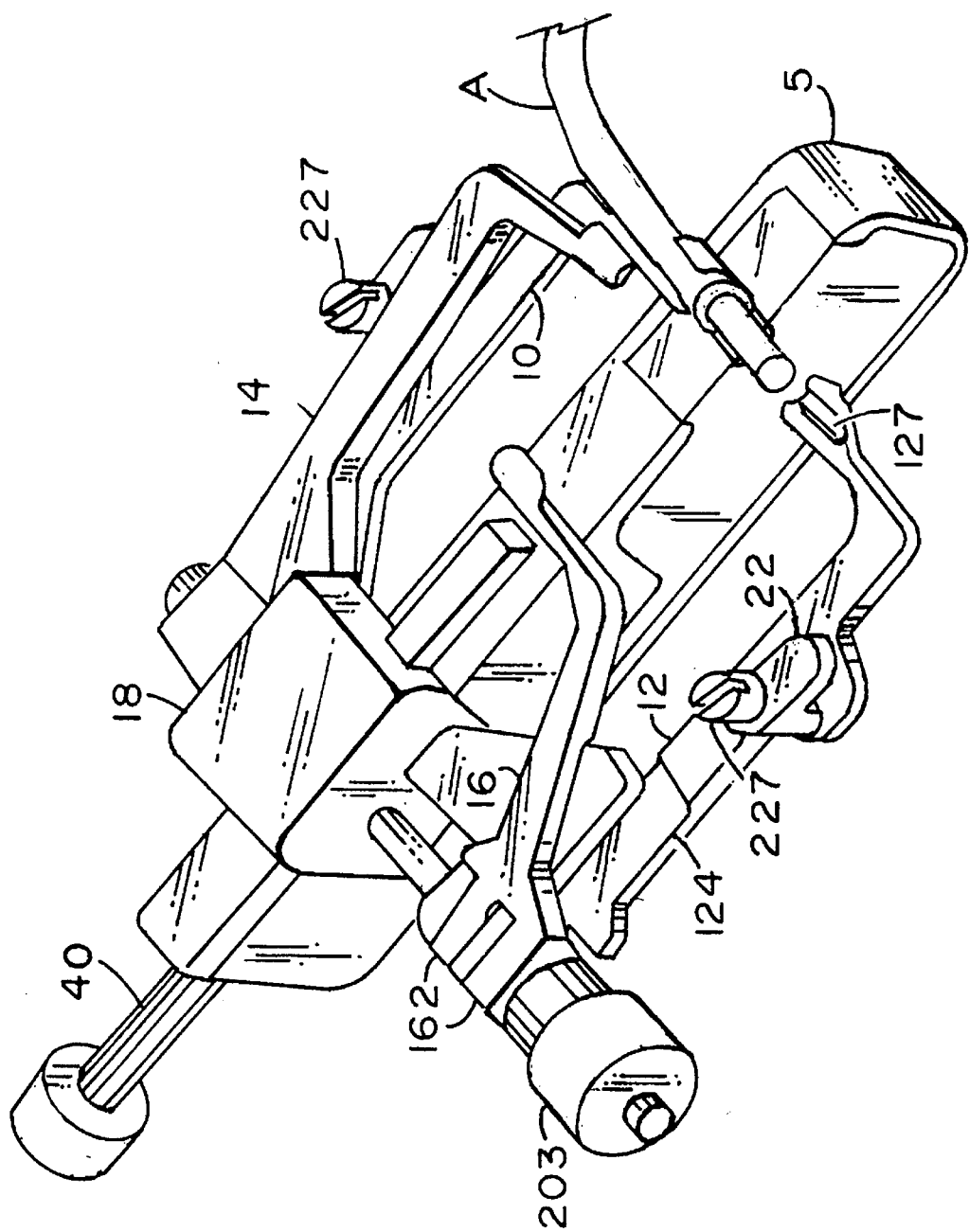
FIG. 1 is a perspective of the clamp of a first embodiment of the present invention showing the bottom housing section 5.

With reference now to the drawings wherein like reference numerals represent identical parts throughout the several views, and more particularly to FIG. 1, reference numeral 1 represents the first embodiment of the clamp of the present invention designed to secure two tubular tissue sections. The energy conduit housing, designated by reference numeral 2 (FIG. 8), is mounted to the clamp 1 and retains the energy transmitting conduits which provide energy to weld together the tubular tissue sections grasped by the clamp 1. In the preferred embodiment, the energy housing 2 comprises a top housing section 3 and a bottom housing section 5 mounted to the upper and lower portions of the clamp 1, respectively. The housing sections 3 and 5 are together referred to as an ExoScope™ device in U.S. Pat. No. 4,892,098, the text of which is incorporated herein by reference. (The term ExoScope™ is a trademark of Laser Surge, Inc. and is applied to a preferred energy applying apparatus available from Laser Surge, Inc.) It should be noted that the terms "upper, lower, bottom and top" as used herein are for the reader's reference since clearly, if the orientation of the clamp 1 and housing 2 changes, the designations of these terms will correspondingly change.

Figure 2:
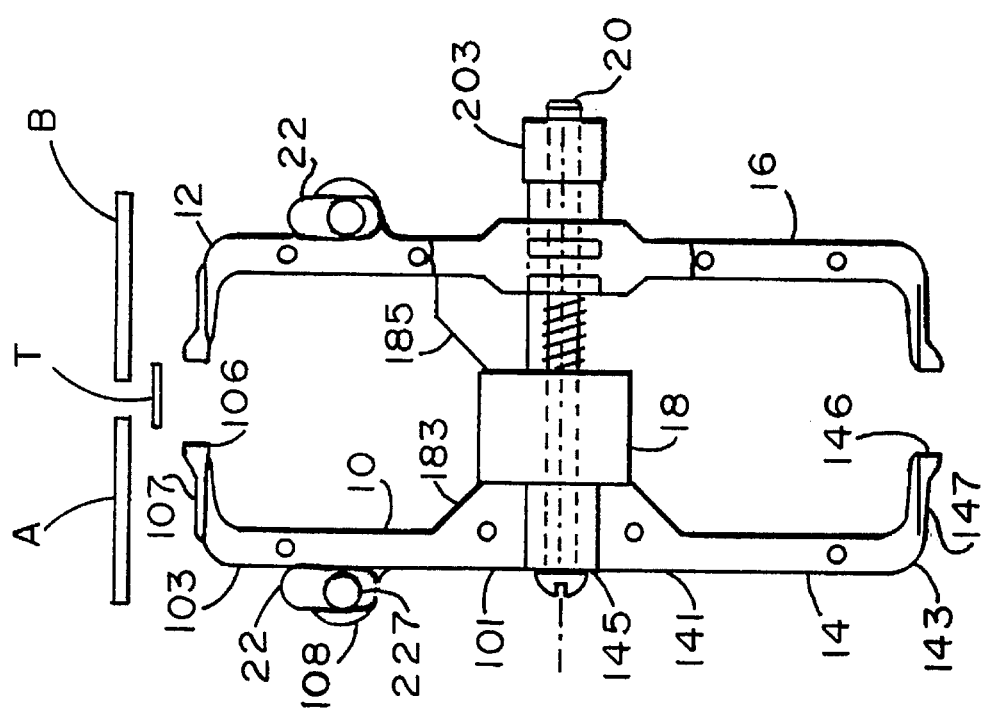
FIG. 2 is a top view of the clamp of the present invention in an open position.

The clamp 1 of the present invention is designed to bring two tubular sections of tissue (e.g. a first or proximal section A and second or distal section B; see FIG. 2) into abutting relationship and securely maintain these sections in this position for a sufficient amount of time for energy to be applied thereto to weld the two sections together. This surgical connection of such hollow tubes to establish or re-establish communication is referred to as an "anastomosis". The clamp 1 effectively provides for successful anastomosis by first firmly and independently grasping each of the tubular sections A and B and sequently bringing these sections A, B into close apposition (abutment). The circumferential grasping of each end of the cut tissue additionally constricts the source of blood flow leading to the wounds. Energy can then be precisely applied around the circumference of the seam formed at the abutment to weld the tubular sections together. The apparatus and method for achieving this sutureless and staple-less anastomosis will now be described in detail.

Figure 3:
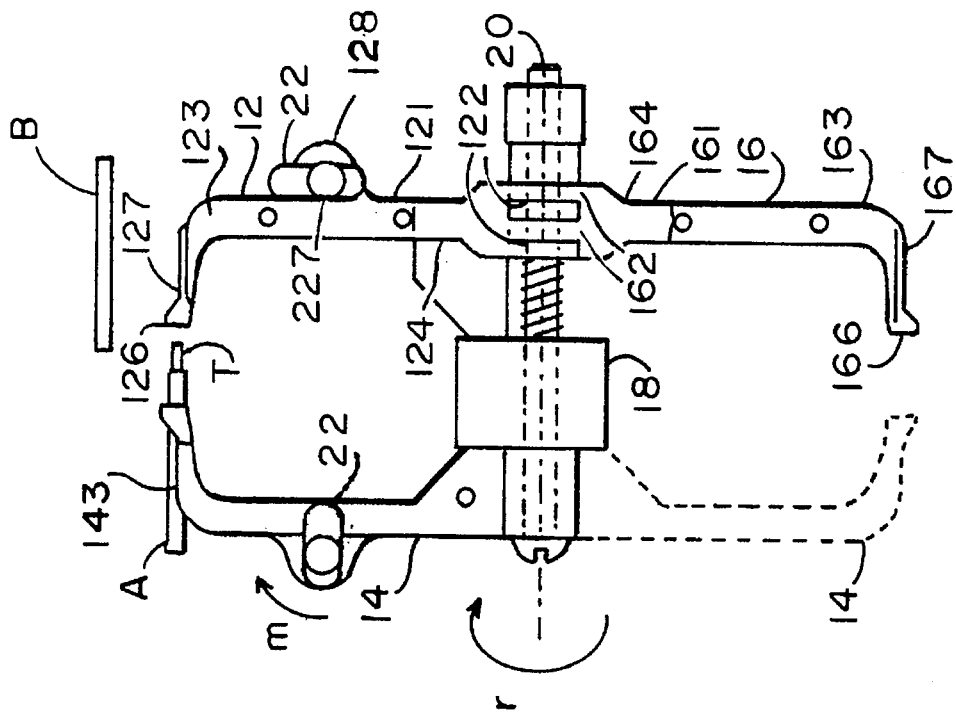
FIG. 3 is a top view of the clamp of the present invention showing the proximal arms in the closed position.

Turning now to FIGS. 2 and 3, clamp 1 has a pair of proximal arms (jaws) comprising a lower proximal arm 10 and an upper proximal arm 14 and a pair of distal arms (jaws) comprising a lower distal arm 12 and an upper distal arm 16. (The terms "proximal, "distal", "lower" and "upper" are used for the reader's reference to differentiate between the arms. Clearly, if the orientation of the clamp changes, these designations will also change.) Each pair of arms is mounted on an axle 20, preferably threaded, for pivotal movement. Axle 20 extends through an aperture in a center post 18 of the base of the clamp. An anchor or retainer 22 is mounted on the lower proximal arm 14 and on the lower distal arm 16 to secure the upper arms 14 and 16 to their respective lower arms 10, 12 in a manner described below.

The lower proximal arm 10 as shown is L-shaped with a rear end 101 connected to center post 18 and an inwardly extending free front end 103. Front end 103 has a longitudinal slot 107 formed in its top surface which preferably decreases in width at a tip portion 106. Ear 108 extends outwardly from a central portion of lower proximal arm 10 and has an aperture formed therethrough to receive a fastener to mount anchor 22. Lower proximal arm 10 is preferably rigidly mounted to axle 20 and to center post 18 so pivotal movement is prevented. However, alternately, lower proximal arm 10 could be pivotally mounted to the axle 20 to allow free rotation.

With continued reference to FIGS. 2 and 3, upper proximal arm 14 is pivotally mounted to axle 20 for pivotal movement with respect to lower proximal arm 10. The upper proximal arm 14 pivots between an open position spaced apart from lower proximal arm 10 (FIG. 2) to a closed position overlying lower proximal arm 10 (FIG. 3). FIG. 3 shows upper proximal arm 14 in dotted line in the open position. In the closed position, portions of the lower surface of upper proximal arm 14 may abut portions of the upper surface of lower proximal arm 10, and preferably, at least the central portions of arms 10 and 14 abut one another in the closed position. A rear end 141 of upper proximal arm 14 includes a tubular bracket 145 which encircles axle 20 for mounting thereon. In one embodiment, upper proximal arm 14 can pivot to an open position up to an arc of approximately 270°; however, a smaller or full 360° pivot is also within the scope of the present invention. Upper proximal arm 14 has an inwardly extending free front end 143 with a longitudinal recess 147 formed in its bottom surface which preferably has a decreased width at tip portion 146, thereby cooperating with free front end 103 of lower proximal arm 10 when in the closed position. That is, recess 147 of upper proximal arm 14 cooperates with longitudinal slot 107 of the top surface of lower proximal arm 10 to form a channel therebetween to receive tubular section A when the proximal arms 14, 10 are in their closed position. Tip portions 146 and 106 of upper and lower proximal arms 14, 10, respectively, have rounded ends which form a narrow circular opening through which tubular section A extends for reasons which will become apparent from the discussion below.

Referring now to FIG. 3, (for clarity, the distal arms 12 and 16 are not labelled in detail in FIG. 2) lower distal arm 12 is pivotally mounted on axle 20 and is illustratively rotatable around an arc of 360°, although other arms are also contemplated. Rear end 121 of lower distal arm 12 has a pair of spaced apart clasps 122 having annular holes to receive axle 20 for mounting thereon. Rear end 121 further includes a recessed surface 124 (on the upper surface of lower distal arm 12) for reasons discussed below. A free front end 123 is substantially identical in configuration to the front end 103 of the lower proximal arm 10 as it has a longitudinal slot 127 in its upper surface preferably terminating in a decreased width portion at tip section 126. Lower distal arm 12 also includes, similar to lower proximal arm 10, an outwardly extending ear 128 having an aperture to receive a fastener for mounting anchor 22.

Upper distal arm 16 is pivotally mounted to lower distal arm 12 for movement between an open position spaced from lower distal arm 12 to a closed position overlying lower distal arm 12. Preferably upper distal arm 16 is pivotable to an arc of approximately 270°; however, clearly upper distal arm 12 can be pivotable along a larger or smaller arc. Upper distal arm 16 includes a rear end 161 having a pair of spaced apart clasps 162 with annular holes through which axle 20 extends for mounting thereon. These clasps 162 are disposed between clasps 122 of lower distal arm 12 as shown in FIG. 3. Front end 163 of upper distal arm 16 is substantially identical to the front end 143 of upper proximal arm 14 in that it includes an inwardly extending portion having a longitudinal recess 167 formed in its bottom surface terminating at tip portion 166 where it preferably has an decreased width. When the arms 16, 12 are closed, longitudinal recess 167 of upper distal arm 16 cooperates with longitudinal recess 127 of lower distal arm 12 to form a channel for receiving tubular tissue section B. Tissue section B protrudes beyond the annular opening formed at the end of cooperating tip portions 126, 166. Upper distal arm 16 also has a recessed portion 164 in its bottom surface in rear end 161.

The base of the clamp includes a central post 18, shown in the drawings shaped as a block, which has a central aperture extending therethrough to receive axle 20. As shown in FIG. 2, the base further includes a distal support 185 and a proximal ear 183 preferably integral with the post 18. Distal support 185 fits within recesses 124 and 164 of lower distal arm 12 and upper distal arm 16, respectively, when the closed distal arms 12, 16 are moved inwardly towards the proximal arms 10, 14 in a manner described below. The top portion 180 (FIG. 5) of the post 18 is adapted to receive top housing section 5 and the bottom portion of post 18 (not shown in the drawings) is adapted to receive the bottom housing section 3.

Axle 20, which is illustratively formed as a threaded screw, extends through the aperture in post 18 and has a spring 201 mounted thereon which is disposed intermediate clasp 122 and post 18. A longitudinal adjustment nut or cap 203 fits over the end of the axis screw 20 and is adapted to be brought into contact with clasp 162 (or alternately clasp 122) of upper distal arm 16, thereby functioning to move closed distal arms 12, 16 towards proximal arms 10, 14 in a manner described in detail below.

Figure 4:
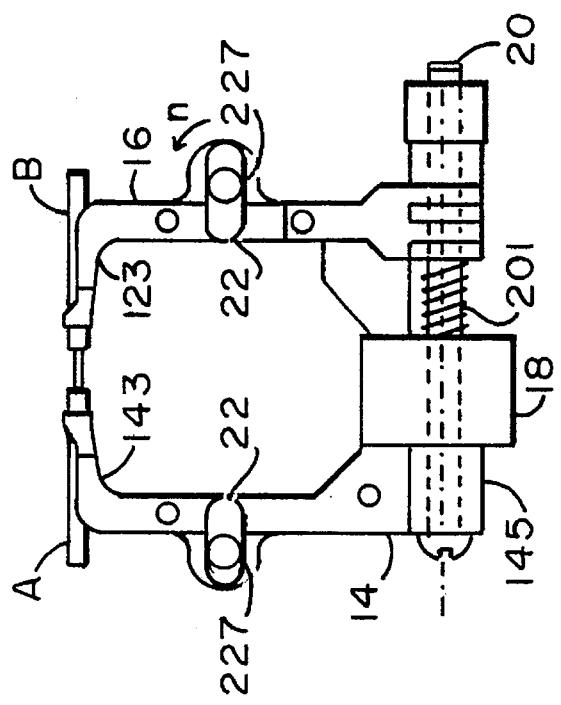
FIG. 4 is a top view of the clamp of the present invention showing both the proximal and distal arms in the closed position.
Figure 7:
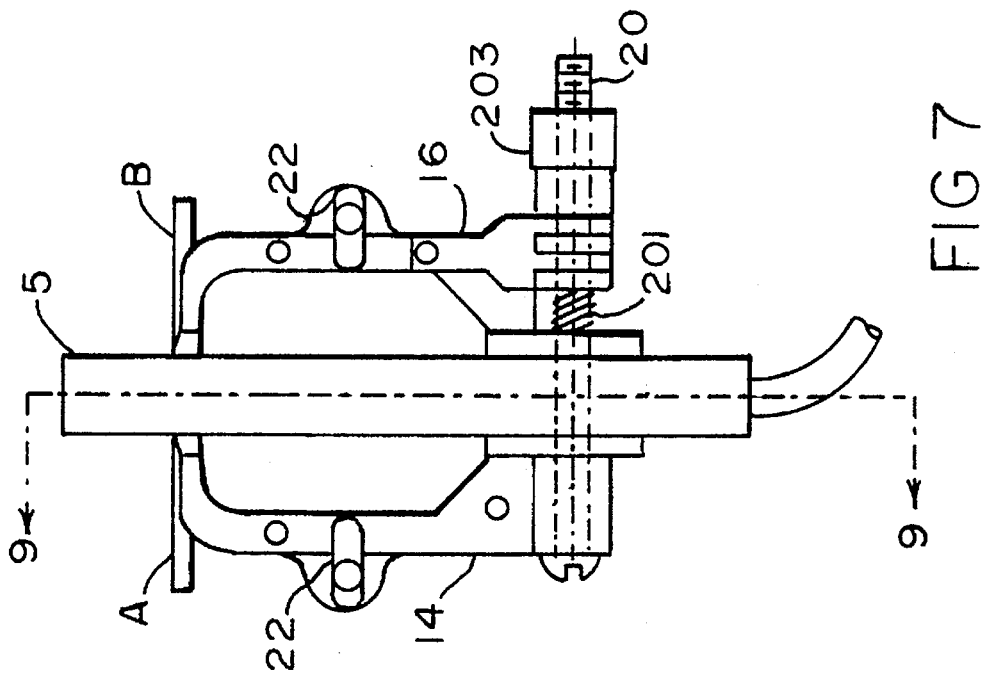
FIG. 7 is a top view of the clamp of FIG. 6 with both the bottom and top housing sections of the energy conduit housing mounted on the clamp.
Figure 6:
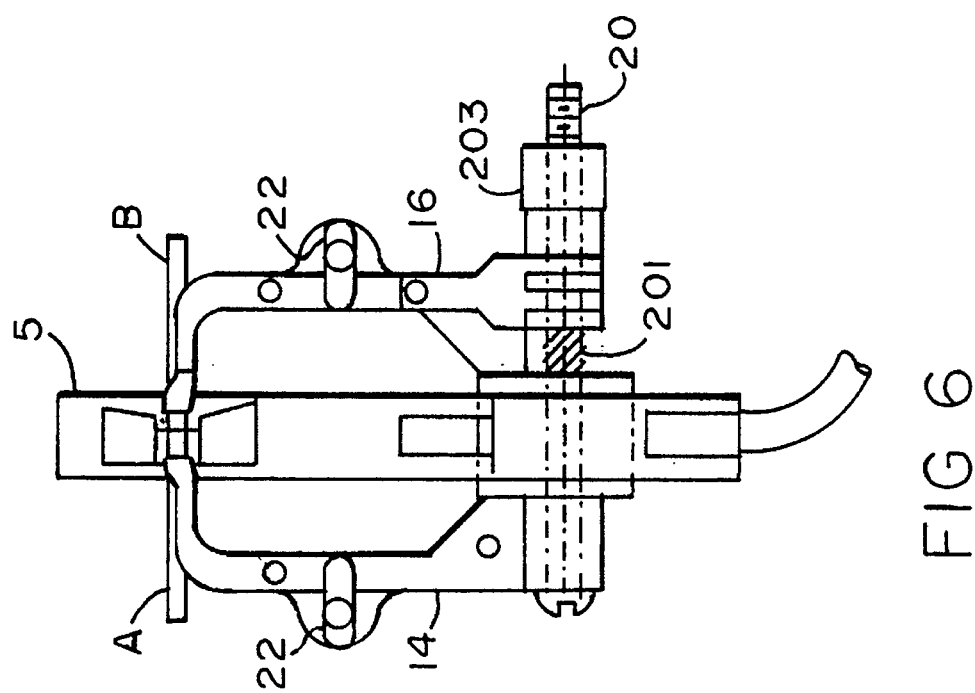
FIG. 6 is a top view of the clamp of the present invention in the closed position showing the bottom housing.

An anchor 22 is swivelably mounted to both ear 108 of lower proximal arm 10 and ear 128 of lower distal arm 12 by a screw 227 (See FIGS. 2–4). Screw 227 extends through an opening formed in the anchor 22 and through the aligned aperture of the respective ear 108, 128. The anchor 22 is illustratively L-shaped in configuration and is pivotable in the direction of arrows m and n (FIGS. 3 and 4) from a resting position substantially parallel to the longitudinal axis of its respective arm 10, 12 to a locking position substantially perpendicular to the longitudinal axis. The anchor 22 has an undercut portion which provides a sufficient gap to receive the respective upper arm 14 and 16 as described below. A conventional nut (not shown) can optionally be mounted to the bottom end of screw 227. The anchor 22 in its locking position compresses the bottom surface of the undercut against the upper surface of the upper arms 14, 16 in the closed position.) Clearly, other means for anchoring the pair of proximal arms and pair of distal arms (e.g. snaps or screws) can be utilized as long as it provides firm securement of the arms.

Figure 8:
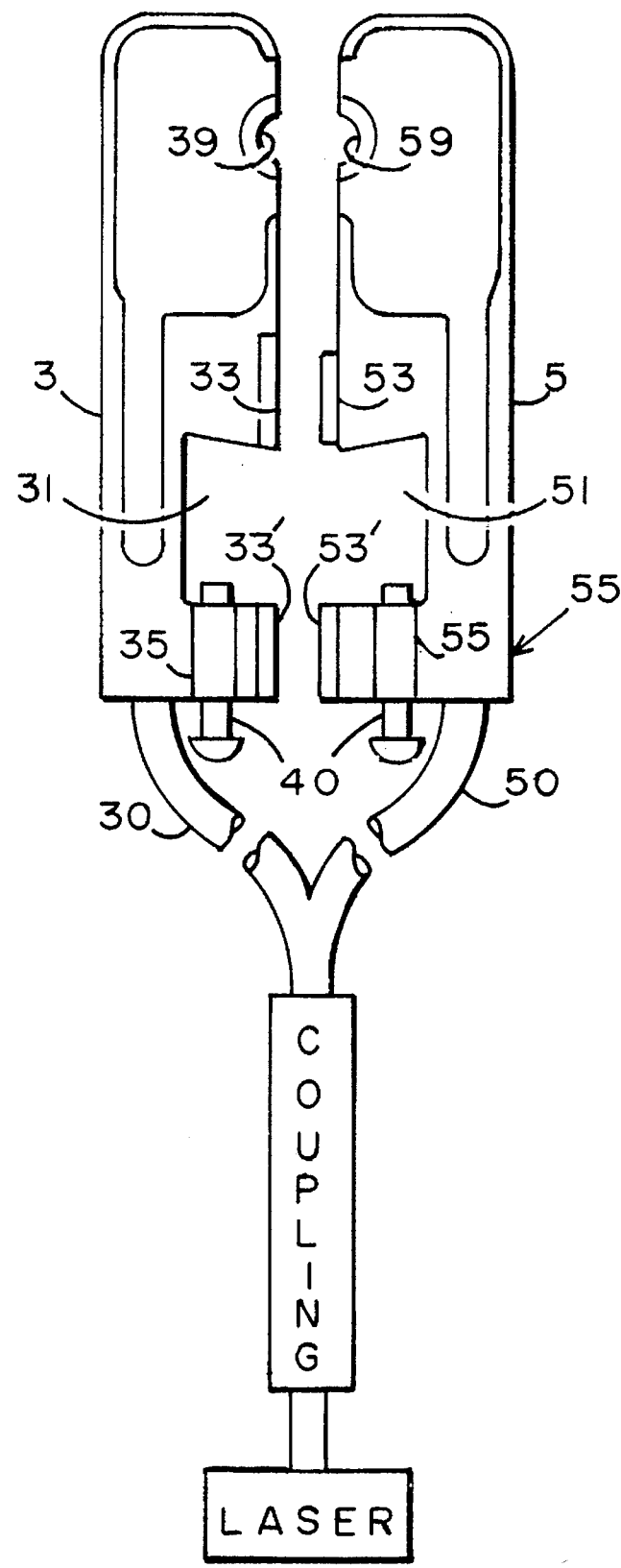
FIG. 8 is a cross sectional view of the top and bottom housing sections of the energy conduit housing.
Figure 9:
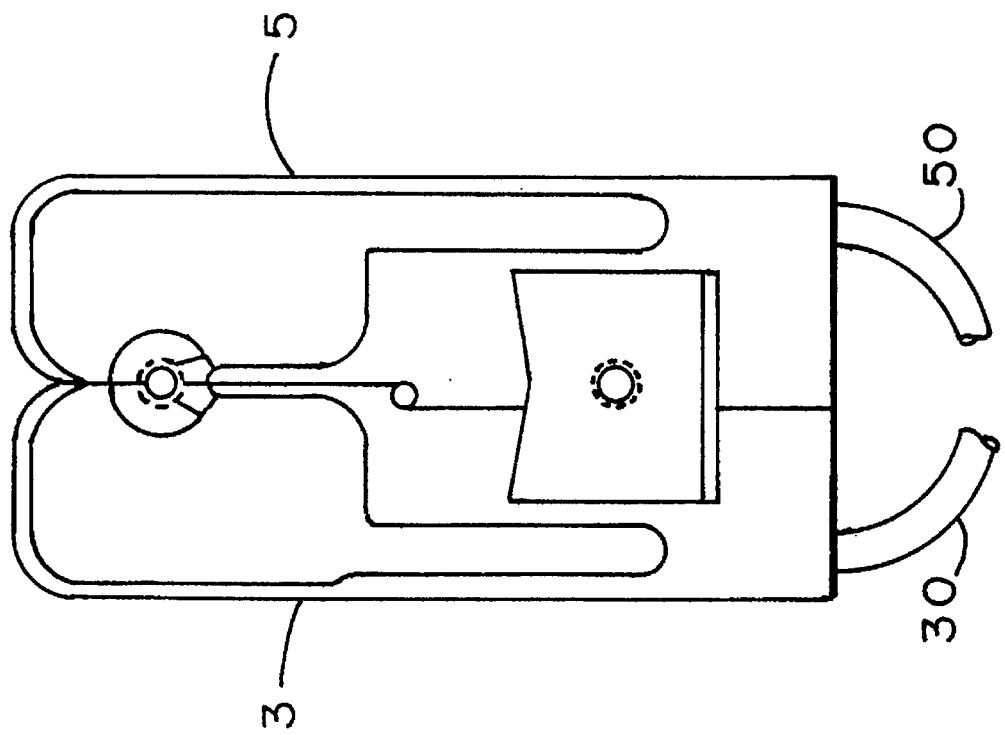
FIG. 9 is a cross sectional view taken along lines 9—9 of FIG. 7.

Turning now to the top housing section 3 and bottom housing section 5 of the energy source housing 2, these housing sections are mounted to opposing sides of clamp 1 and provide the means for applying energy to the seam formed between abutting tubular sections A and B. As noted above, the terms "top" and "bottom" are used for convenience to denote placement on opposing sides of the clamp 1 since the clamp can be re-oriented. As shown in FIG. 8, top housing section 3 includes a central recess 31 to receive the top portion of center post 18, and front and rear longitudinal slots 33, 33' formed on its inner surface. An upper channel 35 extending from the rear of housing section 3 to recess 31 provides for passage of a tightening screw 40. The tightening screw 40 is adapted to be rotated inwardly to press against central post 18 when housing section 3 is mounted thereon to effectively secure the top housing section 3 to clamp 1. A separate channel is spaced apart from upper channel 35 to allow passage of the energy transmitting conduits in channel 30.

Bottom housing section 5 is substantially identical in configuration to top housing section 3 except it is provided with projections 53, 53' on its inner surface instead of longitudinal slots 33, 33'. The projections 53, 53' are adapted to engage slots 33, 33', respectively, of top housing section 3 when bottom housing section 5 is fitted over top portion 180 of post 18 to secure the two housing sections together. Of course, alternate ways to connect the two housing halves can be utilized. Similar to top housing section 3, bottom housing section 5 includes a channel 55 to receive a screw 40 for tightening the housing section 5 against central post 18. A separate channel spaced from channel 55 receives a conduit 50 for transmitting energy.

Both housing sections 3, 5 include a semicircular recessed portion 39, 59, respectively, through which the energy is transmitted. The recesses 39 and 59 cooperate to form a circular enclosure for the annular seam S of the abutting tubular sections A and B when the housing sections 3, 5 are mounted to opposing sides of clamp 1 and projections 53, 53' are interfitted within longitudinal slots 33, 33'. Although the housing 2 is illustrated as comprising two discrete sections 3 and 5, clearly a single housing with hinged sections could alternatively be provided.

The channels 30, 50 for the energy conduits extends through both bottom and top housing sections 3, 5, and in a preferred embodiment comprise a series of multiple fibers radially directing light with respect to semicircular recessed portions 39 and 59 in order to transmit electromagnetic energy simultaneously along the entire circumference of the seam S formed at the abutment of tubular sections A and B. The fibers preferably terminate before recesses 39, 59 so they are adjacent, but not contiguous, to the seam S. Electromagnetic energy can travel radially to directly affect the abutted tissue or alternately a lens system such as a prism or mirror could be positioned at an angle to the seam so that, in the case of laser energy, incoming laser light will be directed by the lens system onto the seam. With continued reference to FIG. 8, the conduits 30, 50, each containing multiple optical fibers, extend rearwardly from the housing sections 3, 5, to a coupler where the proximal ends of the multiple fibers interface with light emitted from a single standard optical fiber from a laser or are coupled directly to the laser itself. Block diagrams here illustrate coupling to a single optical fiber from an external source of electromagnetic energy. The aspects of generating the electromagnetic energy from the external source are known in the art and beyond the scope of the present invention as is the coupling of a single fiber to a laser.

With reference to FIGS. 2–7, the operation of the clamp 1 of the present invention will now be described. FIG. 2 shows clamp 1 with both upper distal arm 14 and upper proximal arm 16 in the open position. Note that anchor 22 is disposed along ear 108 in a position substantially parallel to the longitudinal axis of lower proximal arm 10 to avoid interference with movement of upper proximal arm 14 to the closed position. As shown in FIG. 3, tubular tissue section (proximal section) A is placed longitudinally in the slot 107 of lower proximal arm 10 and the upper proximal arm 14 is then pivoted in the direction of arrow r to its closed position to overlie lower proximal arm 10. Tubular section A is thus firmly fitted within the channel formed between cooperating slot 107 of lower proximal arm 10 and recess 147 of upper proximal arm 14. Anchor 22 is then rotated in the direction of arrow m to its locking position, substantially perpendicular to the longitudinal axis of the lower proximal arm 10, so that it holds the proximal arms 10, 14 together in their closed position. Proximal arms 10 and 12 provide sufficient pressure to effectively function to reduce or even stop the bleeding.

Once tubular tissue section A is securely clamped by proximal arms 10, 14, the other tubular section (distal section) B is placed within slot 127 of lower distal arm 12 and upper distal arm 16 is pivoted to its closed position to overlie lower distal arm 12 (FIG. 4). Anchor 22, attached to ear 128 of lower distal arm 12, is subsequently rotated (see arrow n of FIG. 4) to its perpendicular locking position to secure the distal arms 10, 16 together to thereby firmly grasp tubular section B within the channel formed between the cooperating slot 127 of lower distal arm 12 and recess 167 of upper distal arm 16. Distal arms 12 and 16 also function to reduce or stop the bleeding.

Figure 5:
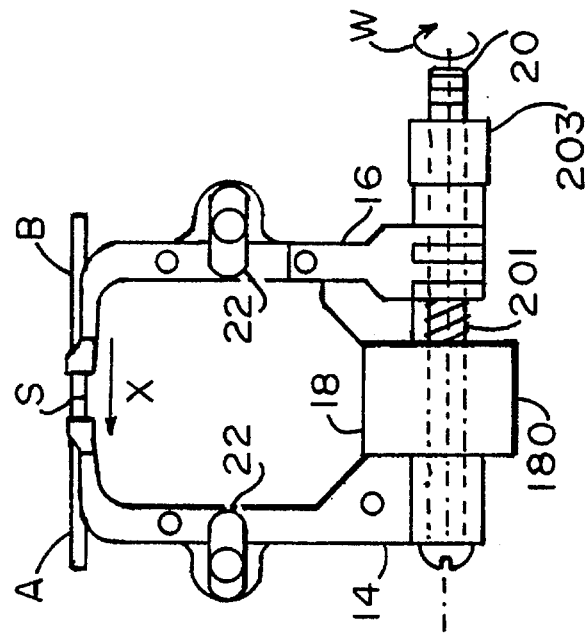
FIG. 5 is a top view of the clamp of the present invention in a closed position where the distal arms have been moved longitudinally to approximate the ends of the tubular tissue sections.

After securement of both the proximal and distal tubular sections A, B, in their respective arms, adjustment nut 203 on threaded axle 20 is rotated clockwise (in the direction of arrow w of FIG. 5). This rotation moves nut 203 in the direction of arrow x to abut clasp 162. Continued rotation of abutting nut 203 thus moves distal arms 12, 16 longitudinally along axle 20 toward the proximal arms 10,1 4 in the direction of arrow x, thereby compressing spring 201. Longitudinal movement of distal arms 12, 16 carries the grasped tubular section B in the same direction to bring it into apposition (abutment) with tubular section A to form seam S. Apposition preferably requires that the edges of sections A and B are compressed. Achievement of this close apposition and the ability of the clamp 1 of the present invention to hold these tubular sections in abutment enables effective anastomosis of these tubular sections when energy is applied to the seam.

After approximation of the tubular sections A, B by the arms of clamp 1, the bottom housing section 5 is positioned so that the seam S lies in correct alignment for tissue welding. Recess 31 of lower housing section 3 is fitted over a bottom portion of center post 18 of claim 1 (FIG. 6) and secured in position by turning the screw 40 at the back of the housing section 3 to tighten it against post 18. Recess 39 thus encloses half of the circular seam S. The upper housing section 3 is then placed over clamp 1 so that recess 51 is fitted over the top portion 180 of post 18 and projections 53, 53' engage longitudinal slots 33, 33' respectively, of lower housing portion 3. Recess 59 thereby encloses the other half of circular seam S. Similar to bottom housing section 5, top housing section 3 is locked into position by tightening screw 40 against post 18. Positioning of the housing portions 3 and 5 as thus described ensure that the seam S is fully encircled to provide precise delivery of energy.

After interfitting the housing sections 3, 5, the external energy source is operated to transmit a selected dosage of energy for a predetermined time period. The energy travels through conduits 30 and 50 and is delivered radially, to thereby apply energy simultaneously around substantially the entire circumferential seam S formed at the abutment of tubular sections A and B. The energy thereby functions to weld tubular sections A and B together along seam S to provide an effective and improved anastomosis.

While the exact physiologic mechanism of the energy weld is not fully understood, tissue welding is achieved through the controlled application of energy to the anastomastic site to produce a uniform thermal effect which causes the two sides to bind together. That is, the energy thermally induces intrinsic tissue changes (e.g. alterations in tissue collagen and other acellular proteins) as the energy is converted into thermal energy which lead to strong bonds between tissue.

Although any energy transmissible through the conduits could be used, in a preferred embodiment where the vas deferens are to be welded, the Neodymium Yttrium Aluminum Garnet (Nd:YAG) laser such as Sharplan 2100 Nd:Yag laser or a Cooper Model 8000 Nd:Yag laser is utilized with readily available quartz optical fibers. In this embodiment, the line width of the circumferential welding light can be as narrow as 75 microns. For example, in recent experimental trials of this equipment for welding rabbit vas deferens anastomoses, five watts of power from a Nd:Yag laser operating at a continuous mode was applied for 1.5 seconds to successfully provide a uniform circumferential weld at the seam. However, it is clearly within the scope of the present invention to utilize laser energy of different densities and for different time periods, or other sources of electromagnetic energy altogether, to achieve welding of the tubular sections. Such variations may depend on, for example, the type of tissue being welded, the physiologic condition of that tissue, and/or wavelength of energy used.

After application of sufficient energy to weld the tissue sections A, B, the screw 40 is loosened and the top housing section 5 is removed from clamp 1, followed by loosening of the screw 40 to remove the bottom housing section 3. The tubular section B is then removed from distal arms 12, 16 of clamp 1 pivoting anchor 22 to its longitudinal resting position, to free upper distal arm 16. Distal arm 16 is then pivoted away from tubular section B and lower distal arm 12, followed by removal of lower distal arm 12 from tubular Section B. The upper proximal arm 14 is likewise disengaged from the lower proximal arm 10 by rotating anchor 22 to its longitudinal resting position. Upper proximal arm 14 is then pivoted to its open position. Tubular section A is then removed from lower proximal arm 10.

To facilitate securement and approximation of tubular tissue sections, an absorbable stent such as that illustrated in FIG. 1 and designated by reference letter T can optionally be utilized. The stent can be composed of materials which are water soluble and biocompatible such as polyvinyl alcohol (PVA) or polyvinyl pyrrolidine (PVA(PVP)). The proximal end of the stent T is inserted into the proximal tubular section A prior to clamping of the proximal arms 10, 14 around tubular section A. After closing and securement of proximal arm 14 by anchor 22, the distal tubular section B is then pulled over the distal end of the stent T. Subsequently, upper distal arm 16 is pivoted to its closed position. The stent T is preferably water soluble so it can advantageously be left in the body after removal of the clamp 1 and will be fully excreted by the body. Likewise, non-soluble stents (e.g. stainless steel wire, teflon, etc.) can be used to assist in apposition and can be removed after welding through natural occurring openings like the fimbriated end of a fallopian tube or the anus or through a small incision in other structures like the vas deferens. Other means can be provided to facilitate or enhance securement and approximation of the tubular tissue sections such as flat surfaces for compressing tissue, teeth or barbs or vacuum parts along the jaws where the tissue is held.

Optionally, a dye substance such as India Ink can be applied to the proximal and distal tubular sections A, B adjacent the seam to act as an exogenous chromophore to increase energy absorption into the anastomotic edges, thereby enhancing tissue welds and minimizing collateral thermal damage. This advantageously allows use of reduced power settings. Other exogenous chromophores such as Indocyanine Green dye, fluorescein or endogenous chromophores such as blood can alternately be utilized to facilitate absorption of energy by localizing the energy on the welding site.

The clamp 1 of the present invention can be used in a variety of applications for energy welding of tubular sections of the body. For example, the clamp can be used for anastomosis of the vas deferens in performing a vasovasostomy (reversal of a vasectomy). In this instance, the proximal and vas deferens are secured within the jaws (arms) of clamp 1, brought into apposition and welded to re-establish communication. The clamp 1 can also be used for welding the fallopian tubes to reverse surgically induced sterility or repair defects. Other uses include the clamping and subsequent energy welding of the ureter, urethra, blood vessels, biliary tissue and other tubular tissue structures. Additionally, the clamp 1 can clearly be used to grasp and bring into opposition other tissue sections that are not hollow. An additional advantage of this apparatus and method for mechanically holding tissue during welding is that it can be used at distant less accessible sites within body cavities as is necessary in minimally invasive endoscopic or laparoscopic surgical procedures.

The apparatus of the present invention can also be used to clamp metal or plastic tubes or prosthetic materials such as Goretex™ or Dacron™ for surgical uses.

A second embodiment of the invention is shown in FIGS. 10–23, wherein reference numeral 300 represents the clamp of the present invention designed to secure two tubular tissue sections.

Figure 10:
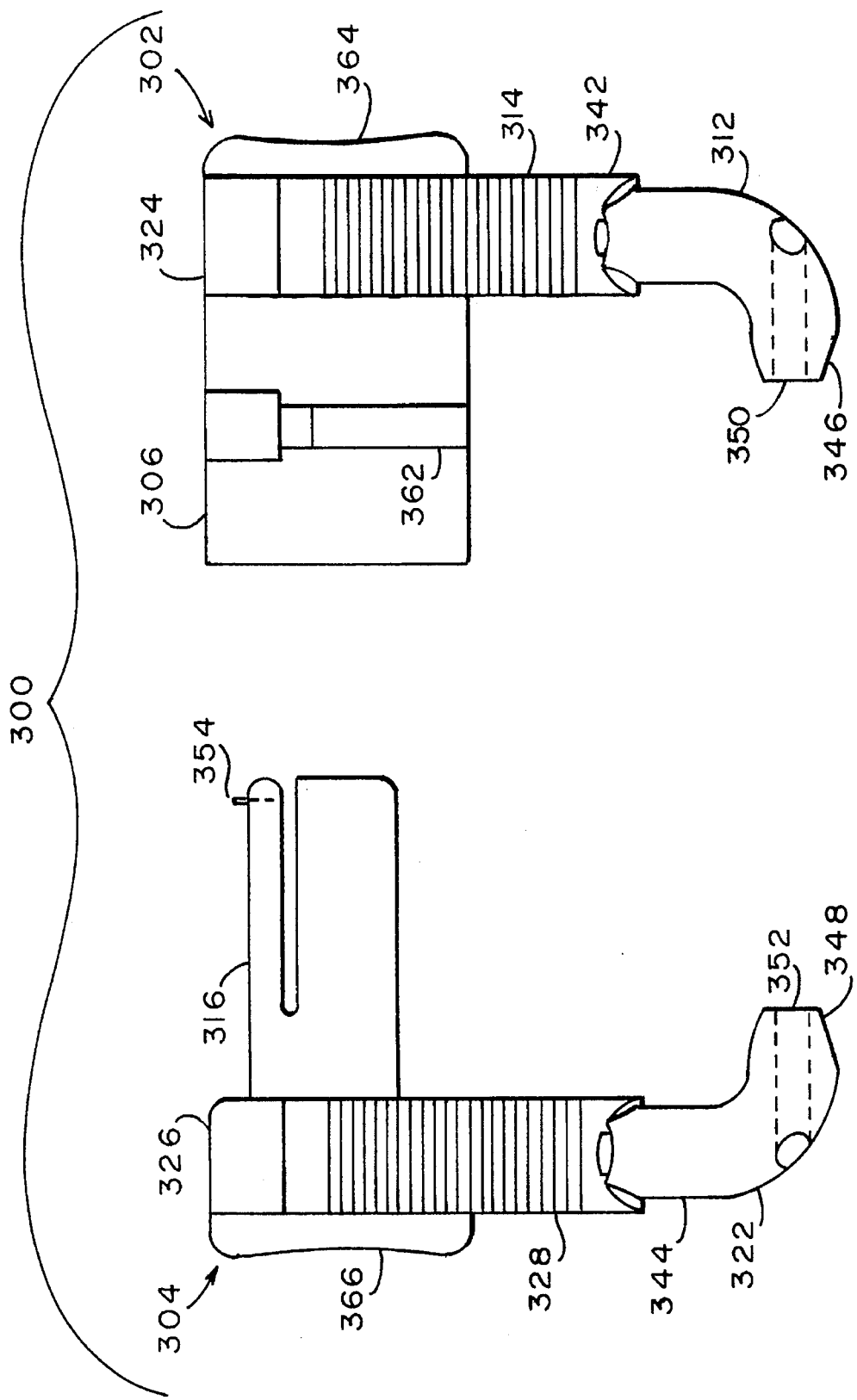
FIG. 10 is a top view of a second embodiment of the present invention showing the two body sections disconnected from each other.
Figure 11:
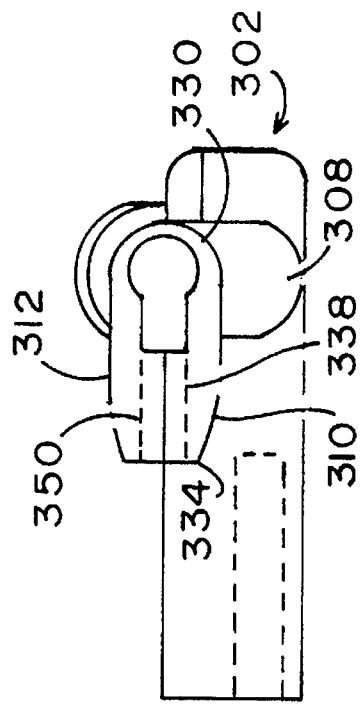
FIG. 11 is a front end view thereof.
Figure 11:
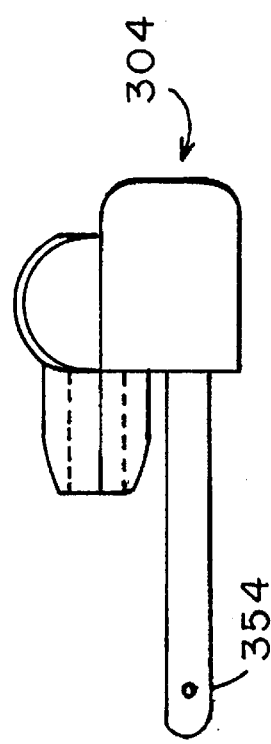
Figure 11:
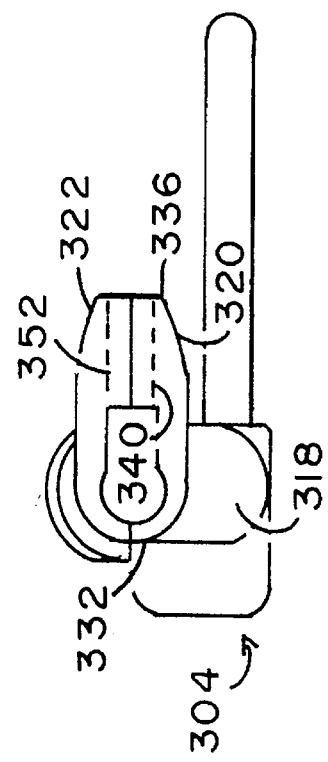
Figure 12:
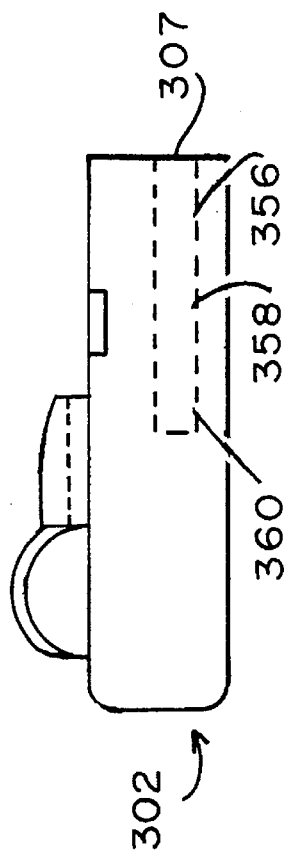
FIG. 12 is a rear end view thereof.

Turning now to FIGS. 10–12 clamp 300 comprises a first body section 302 and a second body section 304. First body section 302 consists of an axle housing 306 having a bore 307 therein and a rigidly affixed lower jaw support 308 terminating in lower jaw 310. Second body section 304 consists of a substantially non-circular axle 316 and a rigidly affixed lower jaw support 318 terminating in lower jaw 320. In a preferred embodiment of the invention bore 307 and axle 316 have substantially rectangular cross sections. Preferably axle housing 306 and axle 316 are provided with finger tabs 364 and 366 respectively, each having a ribbed texture to an exterior surface thereof to facilitate handling.

Figure 14:
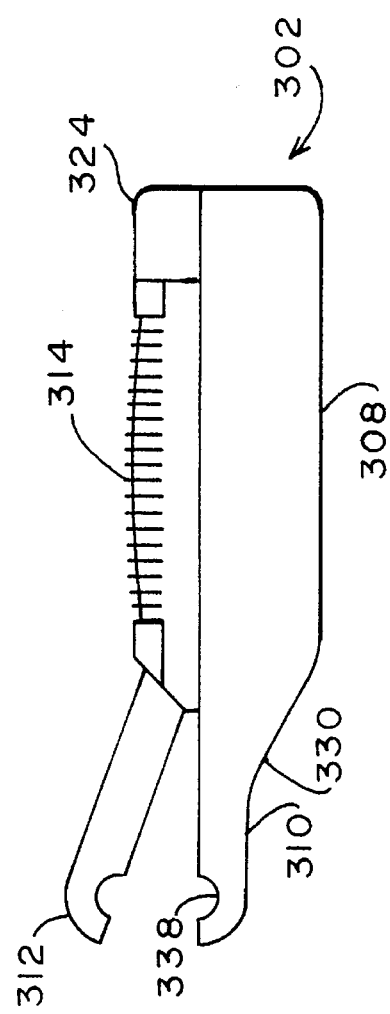
FIG. 14 is a side view of the invention with the jaws in an open and unlocked position.
Figure 16:
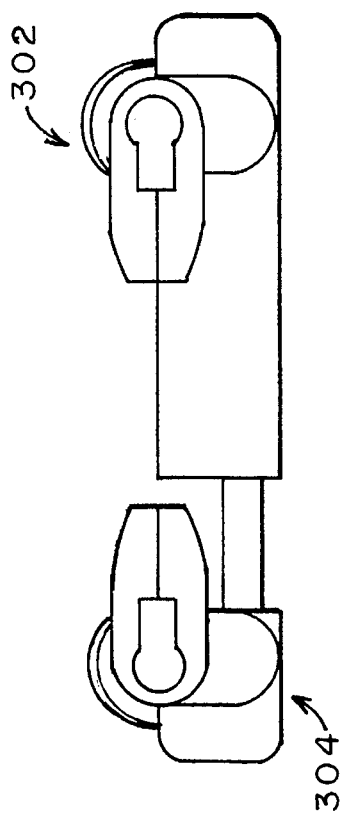
FIG. 16 is a front end view thereof.
Figure 17:
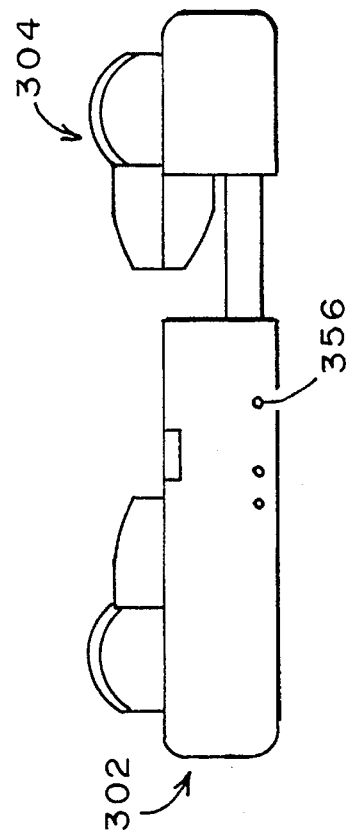
FIG. 17 is a rear end view thereof.
Figure 15:
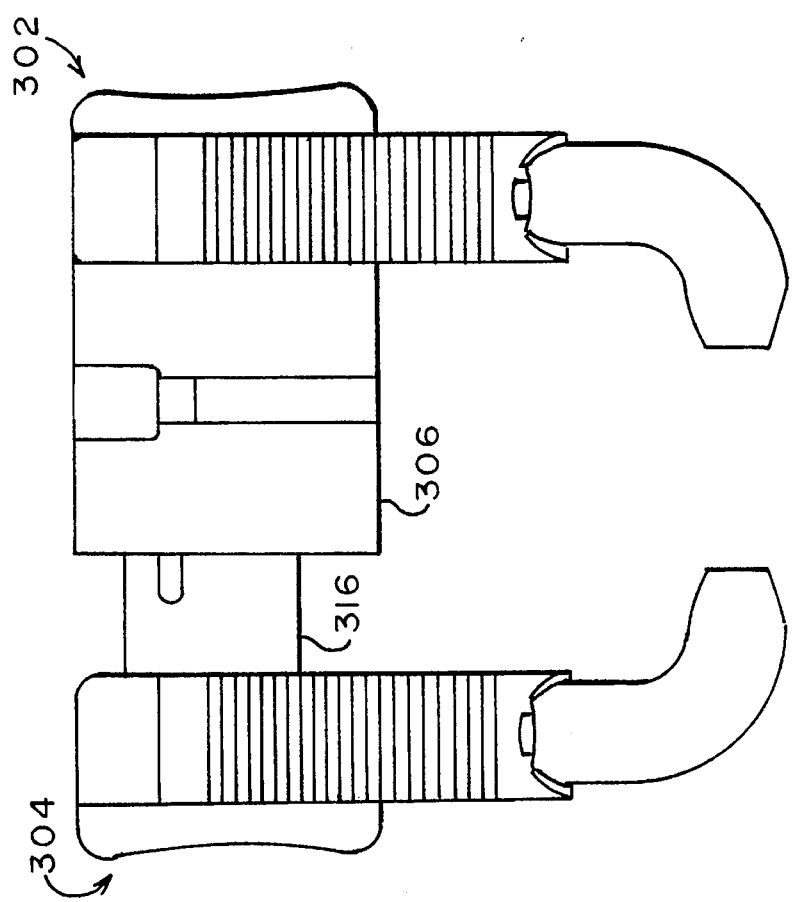
FIG. 15 is a top view of the invention in a stenting position.

Upon lower jaw support 308 and lower jaw support 318 are mounted upper jaw supports 324 and 326 terminating in upper jaws 312 and 322 respectively. Slidable anchor barrels 314 and 328 are mounted on upper jaw supports 324 and 326 respectively. With reference to FIGS. 11 and 14 lower jaws 310 and 320 are L-shaped with respective rear ends 330 and 332 connected to lower jaw supports 308 and 318. Lower jaws 310 and 320 have inwardly extending free front ends 334 and 336 respectively. Lower recesses 338 and 340 extend through and exit lower jaws 308 and 318 from lower front ends 334 and 336 parallel to the axes of axle housing 306 and axle 316.

Upper jaws 312 and 322 are affixed to upper jaw supports 324 and 326 and are pivotable through an arc of at most approximately 270°, typically approximately 180° or approximately 120° and more typically approximately 90°. Upper jaws 312 and 322 are L-shaped with respective rear ends 342 and 344, which are pivotably connected to upper jaw supports 324 and 326, and respective inwardly extending free front ends 346 and 348. Upper tissue recesses 350 and 352 extend from respective upper front ends 346 and 348 back parallel to the axis of axle housing 306 and axle 316 exiting upper jaws 312 and 322 respectively as shown.

Figure 13:
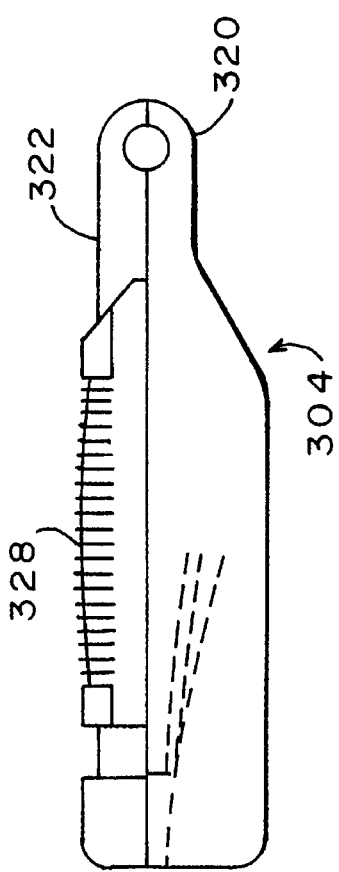
FIG. 13 is a side view of the invention with the jaws in a closed and locked position.

Referring to FIGS. 13 and 14, upper jaws 312 and 322 are pivotable between an open position spaced from lower jaws 310 and 320 to a closed position overlying lower jaws 310 and 320.

Anchor barrels 314 and 328 are slidably mounted on upper jaw supports 324 and 326 respectively. Barrels 314 and 328 are slidable between a first position corresponding to the open position (FIG. 14) and a second position corresponding to the closed position (FIG. 13). Preferably the exterior surfaces of anchor barrels 314 and 328 have a ribbed texture to facilitate handling.

Referring again to FIG. 10, axle 316 may be provided with a detent pin 354 and axle housing 306 may be provided with detent recesses 356, 358 and 360 for precise spacing between body sections 302 and 304. Axle housing 306 may be further provided with grooved slot 362 for receipt of an alignment pin (FIG. 24).

Grooved slot 362 may also be used to hold an ExoScope™ housing (FIG. 25). The ExoScope™ housing shown in FIG. 25 is a one piece unit and operates similar to the two piece housing previously described herein.

The operation of the clamp 300 of the present invention will now be described. FIG. 14 shows first body section 302 of clamp 300 with upper arm 312 in the open position. Note that anchor 314 is disposed along upper jaw support 324 in a position substantially to the rear of body section 302 to avoid interference with the pivotal movement of upper jaw 312.

Body sections 302 and 304 are assembled by sliding axle 316 into the bore 307 of axle housing 306. It will be noted that axle 316 and bore 307 of axle housing 306 are configured and dimensioned to prevent any relative rotational movement of axle 316 and axle housing 306. The initial, or stenting, position is achieved when detent pin 354 engages detent recess 356 (FIG. 17) leaving jaw pairs 310/312 and 320/322 substantially spaced apart from each other.

With upper jaw 312 in the open position, a tubular tissue section A (not shown) is placed longitudinally in tissue recess 338 of lower jaw 310 and upper jaw 312 is pivoted down to the closed position overlying lower jaw 310 such that upper jaw recess 350 covers tissue section A. Tubular section A is thus firmly fitted within the channel formed between cooperating lower tissue recess 338 and upper tissue recess 350. Anchor barrel 314 is then slid toward its locking position partially covering upper jaw 312 thereby holding upper jaw 312 and lower jaw 310 in the closed position.

Once tubular section A is securely clamped by jaws 312 and 310, the other tubular section B (not shown) is placed within lower tissue recess 340 of lower jaw 320 and upper jaw 322 is pivoted to its closed position overlying lower jaw 320 (FIG. 13). Anchor barrel 328 is then slid forward to its locking position partially coveting upper jaw 322 to firmly grasp tubular section B within the channel formed between cooperating lower tissue recess 340 on lower jaw 320 and upper tissue recess 352 on upper jaw 322.

Figure 19:
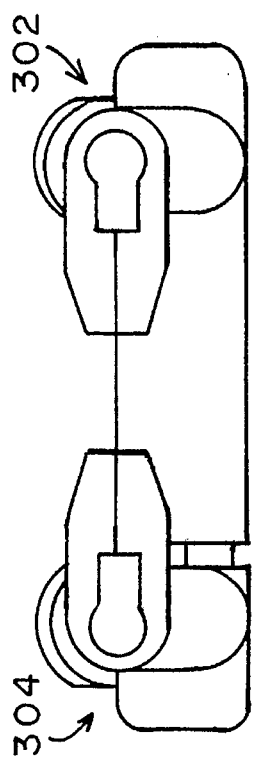
FIG. 19 is a front end view thereof.
Figure 20:
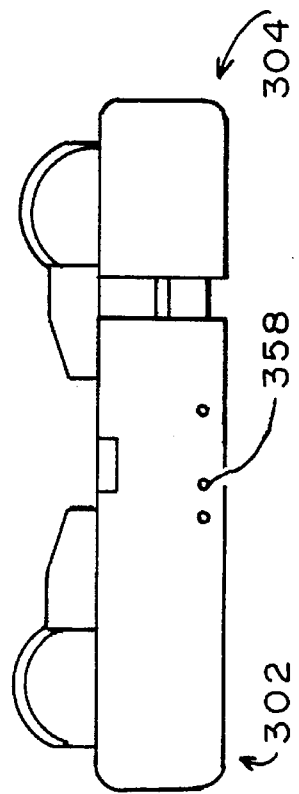
FIG. 20 is a rear end view thereof.
Figure 18:
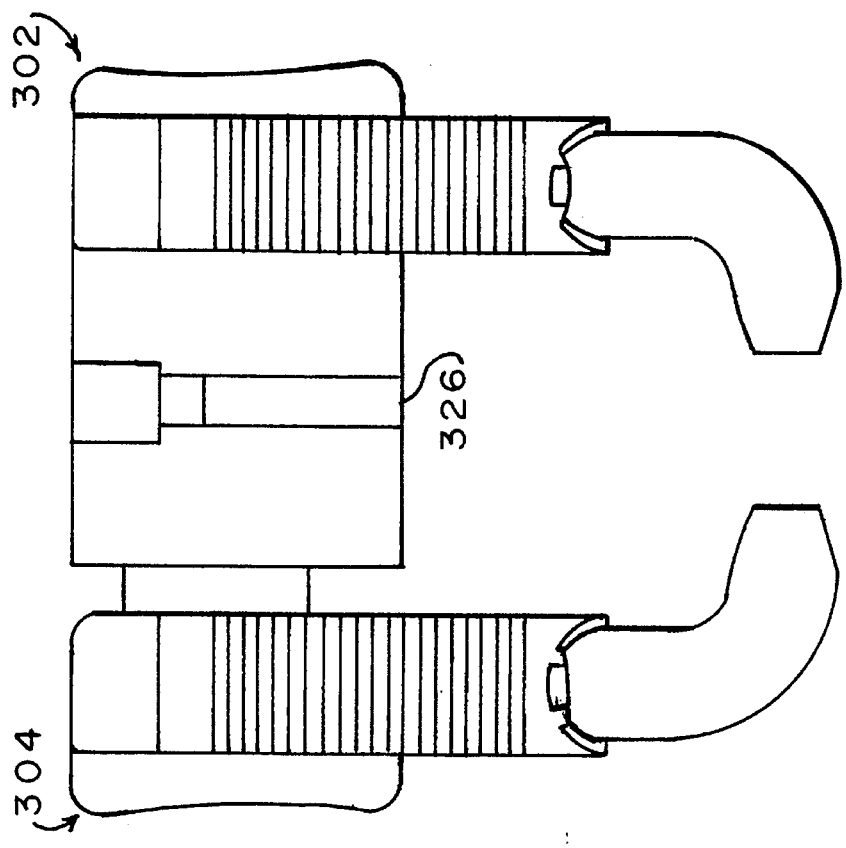
FIG. 18 is a top view of the invention in an alignment position.

After securement of tubular sections A and B in their respective jaws, body sections 302 and 304 are slid together until detent pin 354 engages detent recess 358, i.e. the alignment position as shown in FIGS. 18–20. At this point an alignment tool 400 (FIG. 24) may be slid into alignment pin slot 362 to ensure precise alignment of tubular sections A and B prior to welding. Additionally an absorbable biocompatible stent may be inserted into one tubular tissue section while in the stenting position and then into the opposing tissue section upon movement to the alignment position.

Figure 22:
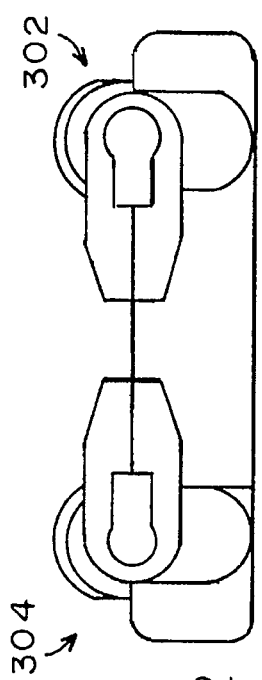
FIG. 22 is a front end view thereof.
Figure 23:
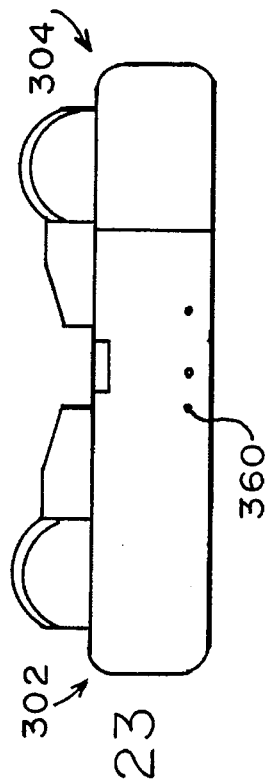
FIG. 23 is a rear end view thereof.
Figure 21:
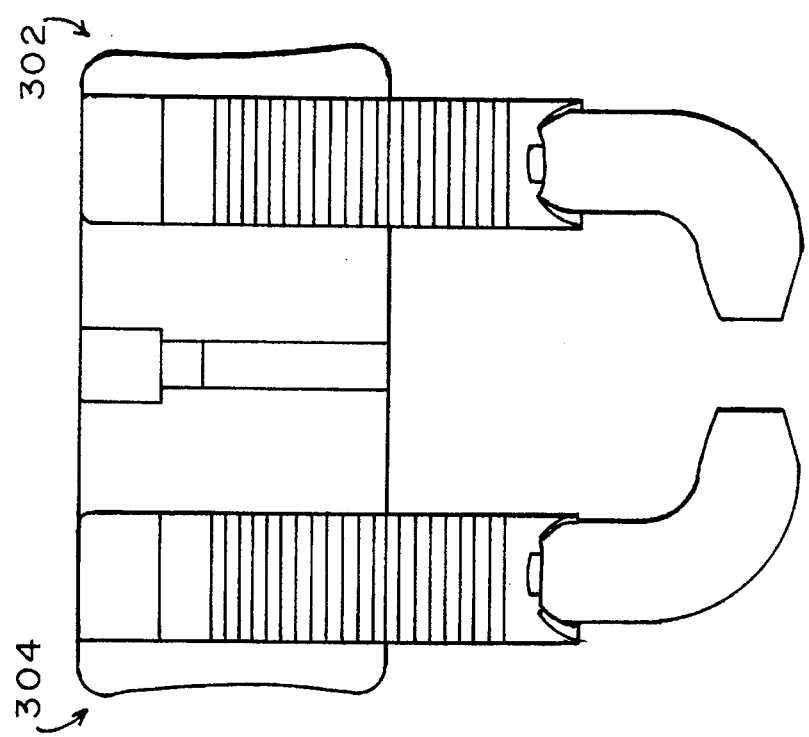
FIG. 21 is a top view of the invention in a weld and suture position.

After the alignment of the two tubular tissue sections, A & B, body sections 302 and 304 may then be slid together such that detent pin 354 engages detent recess 360, i.e. the weld and suture position as shown in FIGS. 21–23. In the weld and suture position the two tubular tissue sections, A & B, are brought into abutment to compress them and form a seam, not shown, which can then be welded or sutured through the process disclosed herein.

Additionally, alignment slot 362 may be used to hold ExoScope™ housing, FIG. 25, for the external energy source.

Obviously, numerous modifications and variations of the present invention are possible in light of the above teachings. It is therefore to be understood that within the scope of the appended claims, the invention may be practiced otherwise then as specifically described herein.

What is claimed is:

1. A surgical apparatus for laser welding first and second body tissue sections comprising:
   a first pair of opposed arms for clamping the first tissue section;
   a second pair of opposed arms for clamping the second tissue section, wherein at least one of said arms of each said pair of arms being pivotably connected to said opposing arm and is pivotable from an open position spaced from said opposing arm through an arc of up to approximately 270° to a closed position overlying said arm;
   means for moving one of said pairs of opposed arms toward the other pair of opposed arms to bring the first and second tissue sections into abutting relationship to form a seam; and
   means for transmitting laser energy to the seam to weld together the first and second tissue sections.

2. A surgical apparatus for laser welding first and second body tissue sections comprising:
   a first pair of opposed arms for clamping said first tissue section;
   a second pair of opposed arms for clamping said second tissue section, at least one of said arms of each said pair being pivotally connected to said opposing arm;
   an axle and a cap mounted to an end of said axle, said arms being mounted substantially perpendicular to said axle, wherein rotation of said cap slides one of said pairs of arms longitudinally along said axle towards said other pair of arms to bring said first and second tissue sections into abutting relationship to form a seam;
   a retainer swivably mounted to one of said arms of each said pair of arms, said retainer having an undercut portion adapted to overlie said opposing arm in said closed position, and further comprising a fastener for tightening said retainer against said arm to secure said opposing arms in said closed position; and
   means for transmitting laser energy to the seam to weld together the first and second tissue sections.

3. A surgical apparatus for laser welding first and second body tissue sections comprising:
   a first pair of opposed arms for clamping said first tissue section;
   a second pair of opposed arms for clamping said second tissue section, at least one of said arms of each said pair being pivotably connected to said opposing arm;
   an axle and a cap mounted to an end of said axle, said arms being mounted substantially perpendicular to said axle, wherein rotation of said cap slides one of said pairs of arms longitudinally along said axle towards said other pair of arms to bring the first and second tissue sections into abutting relationship to form a seam, wherein said axle is aligned substantially parallel to a longitudinal axis of said clamped section to be welded,
   wherein each of said opposing arms has an inwardly directed portion, each said portion of each said arm having a recess formed therein to cooperate with said inwardly directed portion of said opposing arm when said arms are in the closed position to thereby form a channel to receive the respective tissue section; and
   means for transmitting laser energy to the seam to weld together the first and second tissue sections.

4. A surgical apparatus as recited in claim 3, further comprising a center post having an aperture formed therein through which said axle extends.

5. A surgical apparatus for laser welding first and second body tissue sections comprising;
   a first pair of opposed arms for clamping said first tissue section;
   a second pair of opposed arms for clamping said second tissue section, at least one of said arms of each said pair being pivotably connected to said opposing arm;
   means for moving one of said pairs of opposed arms toward the other pair of opposed arms to bring the first and second tissue sections into abutting relationship to form a seam; and
   means for transmitting laser energy to the seam to weld together the first and second tissue sections, wherein said laser energy transmitting means comprises a housing adapted to be placed over said first and second pairs of opposed arms, said housing having a plurality of light transmission elements disposed therein, a distal end of said light transmission elements terminating near said seam and a proximal end of said light transmissive elements adapted to be connected to an external laser source.

6. A surgical apparatus as recited in claim 5, wherein said housing comprises a first housing section adapted to be placed over one surface of said clamping means and a second housing section adapted to be placed over an opposing surface of said clamping means.

7. A surgical apparatus as recited in claim 6, wherein said laser energy transmitting means comprises means for simultaneously transmitting laser energy to substantially the entire circumferential portion of the seam.

8. A surgical apparatus as recited in claim 7, wherein said arms are mounted on an axle, and further comprising a center post disposed on said axle intermediate said pairs of arms, and means for tightening said first and second housing sections against said center post.

9. A surgical apparatus as recited in claim 8, wherein said tightening means comprises a screw extending through an opening in each said housing section wherein rotation of said screw moves said screw inwardly towards said center post to press against said post.

10. A surgical clamp for holding two sections of body tissue together, said clamp comprising;
- a base having first and second pairs of arms joined thereto, said first pair of arms pivotably connected to one another for clamping a first tissue section therebetween;
- said second pair of arms pivotably connected to one another for clamping a second tissue section therebetween;
- means for moving one of said pair of arms towards the other pair of arms to bring the first and second tissue sections into abutting relationship,
- wherein each pair of arms comprises first and second arms, and said first arm of each pair of arms being pivotable from an open position spaced from said second arm to a closed position overlying said second arm;
- means for receiving laser energy transmission means; and
- a retainer pivotally mounted to one of said arms of each pair of arms, said retainer being pivotable to a position overlying said pivotable arm to hold said arms in said closed position.

11. A surgical clamp for holding two section of body tissue together, said clamp comprising:
- a base having first and second pairs of arms joined thereto, said first pair of arms pivotably connected to one another for clamping a first tissue section therebetween;
- said second pair of arms pivotably connected to one another for clamping a second tissue section therebetween;
- means for moving one of said pair of arms towards the other pair of arms to bring the first and second tissue sections into abutting relationship;
- means for receiving laser energy transmission means;
- wherein each pair of arms comprises first and second arms, and said first arm of each pair of arms being pivotable from an open position spaced from said second arm to a closed position overlying said second arm;
- anchor means cooperating with said arms for holding said arms of each pair of arms in said closed position;
- wherein one arm of said first pair of arms is fixedly secured to said base and both arms of said second pair of arms are pivotably mounted to said base;
- wherein both arms of each said pair of arms have inwardly extending portions with a recess formed therein which cooperate with the opposing recess when said arms are in said closed position to form a channel to receive one of said tissue sections.

12. A method for surgically welding two tissue sections comprising:
- clamping a first tissue section in a first clamping portion;
- clamping a second tissue section in a second clamping portion;
- moving one of the clamped tissue sections into abutting relationship with the other tissue section;
- positioning laser energy transmission means adjacent said first and second clamping portions;
- applying laser energy through said transmission means to the seam formed at the abutting portion of the tissue sections to weld them together, wherein said step of applying laser energy comprises the steps of:
- placing a first housing on one side of the clamp;
- placing a second housing on the opposing side of the clamp to engage the first housing; wherein each of said housings has a laser transmissive conduit disposed therein terminating near the seam formed between the two sections; and
- removing the clamp after the tissue sections are laser welded together.

13. A method for surgically welding two tissue sections comprising:
- clamping a first tissue section in a first clamping portion;
- clamping a second tissue section in a second clamping portion;
- moving one of the clamped tissue sections into abutting relationship with the other tissue section;
- positioning laser energy transmission means adjacent said first and second clamping portions;
- applying laser energy through said transmission means to the seam formed at the abutting portion of the tissue sections to weld them together;
- removing the clamp after the tissue sections are welded together; and wherein the clamp includes first and second pairs of opposing arms and said step of clamping the first tissue section comprising the steps of:
- placing a first arm of a first pair of arms on one side of the first tissue section;
- pivoting the second arm of said first pair of arms to overlie the first arm; and
- tightening the first and second arms together to secure the first tissue section.

14. A method as recited in claim 13, wherein the step of clamping the second tissue section comprises the steps of:
- placing a first arm of the second pair of arms on one side of the second tissue section;
- pivoting the second arm of said second pair of arms to overlie the first arm; and tightening the first and second arms together to secure the tissue section.

15. A method as recited in claim 14, wherein the clamping of the tissue sections provides sufficient compression to reduce the bleeding.

16. A method as recited in claim 14, wherein each of said arms are mounted substantially perpendicular to an axle, and the step of moving one of the clamped tissue sections comprises the step of sliding one of said pair of arms towards the other pair of arms longitudinally along the axle.

17. A method for surgically welding two tissue sections comprising:
- clamping a first tissue section in a first clamping portion;
- clamping a second tissue section in a second clamping portion;
- moving one of the clamped tissue sections into abutting relationship with the other tissue section;
- positioning laser energy transmission means adjacent said first and second clamping portions;
- applying laser energy through said transmission means to the seam formed at the abutting portion of the tissue sections to weld them together, wherein the step of applying laser energy comprises:
- placing a first housing on one side of the clamp;
- placing a second housing on the opposing side of the clamp to cooperate with the first housing;
- wherein each of said housings has a laser transmission conduit disposed therein terminating adjacent the seam formed at the abutment of the two tissue sections; and
- removing the clamp after the tissue sections are laser welded.

18. A method as recited in claim 17, further comprising the step of tightening the housing against the clamp.

19. A method as recited in claim 18, further comprising the step of applying laser energy simultaneously around substantially the entire circumference of the seam.

20. A method as recited in claim 19, further comprising the step of adding a chromophore to the region adjacent the seam prior to applying laser energy to facilitate laser welding.

21. A method as recited in claim 20, wherein the step of removing the clamp comprises the step of loosening the tightening means to release the first and second arms of each pair of arms and pivoting the second arms away from the respective opposing first arm to an open position.

22. A surgical apparatus for joining first and second tissue body sections comprising:
a) a first pair of opposed arms for clamping the first tissue section;
b) an axle mounted substantially perpendicular to said first pair of opposed arms on one end of said first pair of opposed arms;
c) a second pair of opposed arms for clamping the second tissue section;
d) an axle housing mounted on an end of said second pair of opposed arms for slidable engagement with said axle;
e) wherein at least one of said arms of each said pair being pivotably connected to said opposing arm for movement from an open position spaced from said opposing arm through an arc of at most approximately 270° to a closed position overlying said opposing arm; and
f) means for moving one of said pair of opposed arms toward said other pair of opposed arms to bring said first and second tissue sections into abutting relationship to form a seam;
g) one or more detent holes located on an interior surface of said axle housing; and
h) a protrusion on said axle engagable with said detent holes for precise spacing of said first and second opposed pairs of arms.

23. The surgical apparatus as recited in claim 22 wherein:
a) a first detent hole corresponds to a stenting position,
b) a second detent hole corresponds to an alignment position; and
c) a third detent hole corresponds to a weld and suture position.

24. The surgical apparatus as recited in claim 22 wherein said axle is bifurcated into first and second longitudinal sections, one of said sections being flexible with respect to said other section and having said protrusion at one end thereof.

25. A surgical apparatus for welding or otherwise joining two tissue body sections comprising: a first and a second detachable body section,
a) said first body section including
i) an axle housing and a pair of opposed arms substantially perpendicular to said axle housing,
ii) said axle housing having a first detect recess corresponding to a stenting position, a second detent recess corresponding to an alignment position and a third detent recess corresponding to a weld and suture position,
iii) said pair of opposed arms including a lower jaw support terminating in an L-shaped inwardly facing lower jaw and an upper jaw support mounted on said lower jaw support, terminating in an pivotable L-shaped inwardly facing upper jaw,
iv) said inwardly facing upper and lower jaws having recesses extending through said jaws parallel to said axle housing,
v) said first body section further including an anchor member consisting of a slidable anchor barrel overlying said upper jaw support and slidable over said support from a first position leaving said upper jaw uncovered to a second position coveting a portion of said upper jaw,
vi) said axle housing further including a mounting groove substantially parallel to said pair of arms;
b) said second body section including:
i) an axle slidable within said axle housing and having a detent projection for engagement with said detent recesses,
ii) a second pair of opposed arms mounted substantially perpendicular to said axle,
iii) said pair of opposed arms including a lower jaw support terminating in an L-shaped inwardly facing lower jaw and an upper jaw support mounted on said lower jaw support, terminating in a pivotable L-shaped inwardly facing upper jaw,
iv) said inwardly facing upper and lower jaws having recesses extending through said jaws parallel to said axle housing,
v) said second body section further including an anchor member consisting of a slidable anchor barrel overlying said upper jaw support and slidable over said support from a first position leaving said upper jaw uncovered to a second position covering a portion of said upper jaw, said first body section being slidably engagable with said second body section to bring the first and second tissue sections into abutting relationship to form a seam.

26. A method for holding first and second tissue sections of tissue in close approximation for laser welding, comprising:
placing a first end of a stent inside a first tissue section and clamping the first section of the tissue with the stent in place between a first pair of jaws of a clamp;
placing a second end of the stent in the second tissue section and clamping the second section of the tissue and the stent between a second pair of jaws of the clamp and
moving one of said pair of jaws towards the other pair of jaws to bring the two tissue sections into abutting relationship.

27. A method as recited in claim 26, wherein said jaws are mounted on an axle, and the step of moving one pair of jaws comprises the step of sliding said pair of jaws longitudinally along said axle.

28. A method as recited in claim 26, wherein said first tissue section is positioned in a recess in said first clamping portion and said second tissue section is positioned in a recess in said second clamping portion.

29. A method as recited in claim 26 further comprising applying laser energy to the seam formed at the abutting portion of the tissue sections to weld them together.

30. A method as recited in claim 29, wherein the stent comprises a bioabsorbable material and remains in the welded tissue sections after removal of the clamp.

31. A method as recited in claim 29, wherein the stent is removable after the tissue sections are welded.

32. A method as recited in claim 31, further comprising the step of anchoring the opposing jaws of each pair of jaws to one another to secure the jaws together.

33. A method as recited in claim 32, wherein the clamping of the tissue sections provides sufficient compression to reduce the bleeding.

* * * * *